United States Patent
Aoki et al.

(10) Patent No.: US 6,245,931 B1
(45) Date of Patent: Jun. 12, 2001

(54) PROCESS FOR PRODUCING ACRYLONITRILE OR METHACRYLONITRILE

(75) Inventors: Kunitoshi Aoki, Shinagawa-ku; Satoru Komada, Yokohama, both of (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 0 days.

(21) Appl. No.: 08/604,323

(22) Filed: Feb. 21, 1996

(51) Int. Cl.⁷ ................................................. C07C 253/24
(52) U.S. Cl. .............................................................. 558/324
(58) Field of Search ................................... 558/319, 314, 558/315, 324

(56) References Cited

U.S. PATENT DOCUMENTS

| | | | |
|---|---|---|---|
| 4,162,234 | * 7/1979 | Grasselli et al. | 252/432 |
| 4,167,494 | 9/1979 | Grasselli et al. | 252/432 |
| 4,190,556 | 2/1980 | Grasselli et al. | 252/432 |
| 5,071,814 | 12/1991 | Sasaki et al. | 502/212 |
| 5,093,299 | 3/1992 | Suresh et al. | 252/432 |
| 5,134,105 | * 7/1992 | Paparizos et al. | 502/205 |

* cited by examiner

*Primary Examiner*—Floyd D. Higel
*Assistant Examiner*—Ebenezer Sackey
(74) *Attorney, Agent, or Firm*—Pennie & Edmonds LLP

(57) ABSTRACT

Disclosed is a process for producing acrylonitrile from propylene, or methacrylonitrile from isobutylene by ammoxidation using an improved catalyst composition comprising an oxide catalyst represented by the formula: $Mo_mBi_bFe_fNi_nQ_qA_aE_eO_x$, wherein Q is a mixture of chromium and indium, A is at least one element selected from potassium, rubidium and cesium, E is at least one element selected from manganese magnesium, zinc, cerium, sodium and phosphorus, and m is a number of from 10 to 14, b is a number of from 0.1 to 3, f is a number of from 0.1 to 3, n is a number of from 4 to 10, q is a number of from 0.1 to 2, a is a number of from 0.01 to 0.5, e is a number of from 0 to 3, and x is a number determined by the valence requirements of the other elements present, and a silica carrier having the oxide catalyst supported thereon, wherein the silica carrier is present in an amount of from 40 to 60% by weight, based on the total weight of the oxide catalyst and the silica carrier. With the oxide catalyst composition of the present invention, the desired acrylonitrile or methacrylonitrile can be produced in high yield.

4 Claims, No Drawings

PROCESS FOR PRODUCING ACRYLONITRILE OR METHACRYLONITRILE

BACKGROUND OF THE INVENTION

1. Field of the Invention

The present invention relates to a process for producing acrylonitrile from propylene, or methacrylonitrile from isobutylene, by ammoxidation. More particularly, the present invention is concerned with a process for producing acrylonitrile or methacrylonitrile by reacting propylene with, or reacting isobutylene with ammonia and molecular oxygen in-the gaseous phase in the presence of an improved ammoxidation catalyst composition comprising a novel oxide catalyst and a silica carrier having the oxide catalyst supported thereon, the oxide catalyst comprising, in specific ratios, oxides of molybdenum, bismuth, iron, nickel, a mixture of chromium and indium, at least one element selected from potassium, rubidium and cesium and optionally at least one element selected from manganese, magnesium, zinc, cerium, sodium, and phosphorous.

2. Discussion of Prior Art

There has been well known a process for producing acrylonitrile from propylene, or methacrylonitrile from isobutylene, by ammoxidation in the gaseous phase, which comprises reacting propylene with, or reacting isobutylene with ammonia and molecular oxygen. This process, which has been widely known as an ammoxidation process, has been practiced on a commercial scale. With respect to catalysts for use in this ammoxidation process, a number of proposals have been made, wherein the catalysts have compositions containing molybdenum, bismuth and iron as essential components.

For example, in Unexamined Japanese Patent Application Laid-Open Specification No. 2-59046, U.S. Pat. No. 5,071,814, Examined Japanese Patent Application Publication No. 40-2532, GB Patent No. 1,434,581, Examined Japanese Patent Application Publication No. 51-6649, GB Patent No. 1,436,475, U.S. Pat. No. 4,190,556, U.S. Pat. No. 4,162,234, U.S. Pat. No. 4,167,494 and U.S. Pat. No. 5,093,299, the so-called multi-component oxide catalysts containing molybdenum, bismuth and iron are disclosed.

The catalysts disclosed in the above-mentioned patent documents have shown various advantageous characteristics. But, in the ammoxidation using these catalysts, the occurrence of side reactions is not effectively suppressed, so that the yield of acrylonitrile or methacrylonitrile is not satisfactorily high.

SUMMARY OF THE INVENTION

With respect to a process for producing acrylonitrile from propylene, or methacrylonitrile from isobutylene by using a multi-component oxide catalyst system comprised of oxides of molybdenum, bismuth and iron, the present inventors have made extensive and intensive studies with a view toward improving the yield of acrylonitrile or methacrylonitrile. As a result, it has unexpectedly been found that by use of a catalyst composition comprising an oxide catalyst, which contains, in addition to molybdenum, bismuth and iron, a mixture of chromium and indium, at least one element selected from potassium, rubidium and cesium and, optionally, at least one element selected from manganese, magnesium, zinc, cerium and phosphorous, in specific ratios, and a silica carrier having the oxide catalyst supported thereon, the desired acrylonitrile or methacrylonitrile can be produced with high selectivity and in high yield. The present invention has been completed, based on this novel finding.

Accordingly, it is a primary object of the present invention to provide a process for producing acrylonitrile from propylene, or methacrylonitrile from isobutylene, by ammoxidation, using an ammoxidation catalyst composition, which enables the desired acrylonitrile or methacrylonitrile to be produced with high selectivity and in high yield.

The foregoing and other objects, features and advantages of the present invention will be apparent from the following detailed description and appended claims.

DETAILED DESCRIPTION OF THE INVENTION

According to the present invention, there is provided a process for producing acrylonitrile or methacrylonitrile, which comprises reacting propylene with, or reacting isobutylene with ammonia and molecular oxygen in the gaseous phase in the presence of an oxide catalyst composition comprising:

(a) an oxide catalyst represented by the following formula:

$$Mo_m Bi_b Fe_f Ni_n Q_q A_a E_e O_x \quad (I)$$

wherein:

Q is a mixture of chromium and indium,

A is at least one element selected from the group consisting of potassium, rubidium and cesium, E is at least one element selected from the group consisting of manganese, magnesium, zinc, cerium, sodium and phosphorus, and m, b, f, n, q, a, e and x are the relative atomic ratios of molybdenum, bismuth, iron, nickel, Q, A, E and oxygen, respectively, wherein m is a number of from 10 to 14, b is a number of from 0.1 to 3, f is a number of from 0.1 to 3, n is a number of from 4 to 10, q is a number of from 0.1 to 2, a is a number of from 0.01 to 0.5, e is a number of from 0 to 3, and x is determined by the valence requirements of the other elements present; and (b) a silica carrier having the oxide catalyst supported thereon, wherein the silica carrier is present in an amount of from 40 to 60% by weight, based on the total weight of the oxide catalyst and the silica carrier.

In the formula (I), m is preferably from 11 to 13, b is preferably from 0.3 to 2, f is preferably from 0.5 to 2.5, n is preferably from 5 to 9, q is preferably from 0.2 to 1.5 and a is preferably from 0.1 to 0.4.

The characteristic feature of the oxide catalyst to be used in the process of the present invention resides in that it contains, as an essential component, component Q consisting of chromium and indium which is effective for achieving not only high selectivity for acrylonitrile or methacrylonitrile but also high reactivity of propylene or isobutylene. In other words, the use of chromium and indium in the form of a mixture thereof (component Q) is extremely effective for producing acrylonitrile or methacrylonitrile in high yield, as compared to the use of chromium alone or indium alone. In component Q, the ratio of chromium to the sum of chromium and-indium is preferably from 0.1 to 0.9, more preferably from 0.3 to 0.7. With respect to the amount (q) of the component Q relative to the amount (f) of iron, it is preferred the ratio of q to the sum of q and f be from 0.1 to 0.7.

Component A is also essential to the catalyst composition to be used in the process of the present invention although the content thereof is very small. Component A is effective for improving the selectivity for acrylonitrile from propylene or for methacrylonitrile from isobutylene. When rubidium, cesium or potassium is used alone as component A, rubidium and cesium are more effective for improving the above-mentioned selectivity than potassium, so that the necessary amount of component A can be reduced by use of rubidium or cesium. When component A is used in an amount exceeding the range as defined herein, the reactivity of propylene or isobutylene is lowered.

The above-mentioned ranges of m, b, f and n representing the relative atomic ratios of the other essential components of the oxide catalyst to be used in the process of the present invention are also important from the viewpoint of providing not only high selectivity but also high reactivity in the ammoxidation conducted by the process of the present invention. If an oxide catalyst having a composition falling outside of the ranges as defined herein is employed for the ammoxidation, the selectivity and/or the conversion will be lowered, leading to a lowering of the yield of the desired acrylonitrile or methacrylonitrile.

Component E which is optionally contained in the oxide catalyst may be used for further improving the reactivity of propylene or isobutylene, or for adjusting the properties of the resultant catalyst composition (such as surface area, pore distribution, particle morphology and density). Phosphorus occasionally imparts an improved abrasion resistance to the catalyst composition to be used in the process of the present invention.

As mentioned above, the oxide catalyst composition to be used in the process of the present invention comprises the oxide catalyst as described above and a silica carrier having the oxide catalyst supported thereon. This form of catalyst composition exhibits excellent fluidity during the ammoxidation using a fluidized bed. When the silica carrier is present in an amount of 40% or more by weight, based on the total weight of the oxide catalyst and the silica carrier, the particles of the resultant catalyst composition exhibit a high abrasion resistance. However, when the amount of the silica carrier is more than 60%, the components of the catalyst are caused to be excessively diluted, leading to a lowering of not only the reactivity of propylene or isobutylene but also the selectivity for acrylonitrile or methacrylonitrile in the ammoxidation.

The ammoxidation catalyst composition to be used in the process of the present invention can be produced by a method comprising the three steps of (1) preparing a slurry of starting materials containing a silica sol and the above-mentioned component metallic elements of the oxide catalyst, (2) spray-drying the slurry thus prepared to obtain a dried catalyst precursor, and (3) subjecting the dried catalyst precursor to calcination.

In step (1) of preparing a slurry of starting materials containing a silica sol and component metallic elements of the oxide catalyst, with respect to the sources of the component metallic elements, there is no particular limitation as long as each of the elements is present in such a form as is soluble or dispersible in water or an aqueous solution of acid, such as nitric acid. Preferably, each of the component metallic elements is present in the form of a salt which is soluble in water or an aqueous solution of acid, such as nitric acid. Preferred examples of sources of elements include an ammonium salt, a nitrate, a chloride, a sulfate and an organic acid salt thereof. More specifically, it is preferred that as a molybdenum source, ammonium heptamolybdate be used, and that each of bismuth, iron, potassium, rubidium, nickel, manganese, magnesium, zinc, chromium, indium, cerium and sodium may be present in the form of a nitrate. When it is intended to incorporate phosphorus in the oxide catalyst, phosphoric acid can be advantageously used as the source of phosphorus. A silica sol is preferably used as the source of silica. It is preferred that the silica sol of high purity, which is substantially free of aluminum, be employed.

A slurry of starting materials can be prepared, for example, as follows: phosphoric acid is first added to a silica sol when the incorporation of phosphorus is intended, and an aqueous solution of ammonium heptamolybdate is then added to the resultant mixture, followed by addition of an aqueous solution of a mixture of nitrates of the remaining component metallic elements, wherein each addition is conducted while stirring.

The resultant slurry of the mixed starting materials usually has a pH value of less than 2. When the slurry has such a pH value, a catalyst composition having excellent properties can be obtained.

The subsequent spray-drying of the above slurry can give spherical fine particles which are suitable for use in a fluidized bed.

In step (2) of spray-drying the slurry prepared in step (1) above, the spray-drying of the slurry can be generally conducted by centrifugation or two-phase flow nozzle method which has been commercially employed, to obtain a dried catalyst precursor. In this instance, it is preferred to use, for example, air which has been heated by indirect contact with steam and/or by using an electric heater, as a heat source for drying. The temperature of the spray dryer at an entrance thereof is preferably 300° C. or less, more preferably from 150 to 250° C.

Preferably, the spray-dried catalyst precursor is subjected to a denitrification treatment before calcination. The denitrification treatment can be conducted at a temperature of from 350 to 450° C. for 0.5 to 2.0 hours.

In step (3) of calcination, for example, the dried denitrified catalyst precursor obtained above is calcined at a temperature of from 500 to 650° C., preferably from 550 to 630° C., to thereby obtain a desired oxide catalyst composition. When the calcination temperature is too low, although the conversion of propylene or isobutylene becomes high, not only does the selectivity for acrylonitrile or methacrylonitrile become low, but the abrasion resistance of the catalyst particles is also decreased. On the other hand, when the calcination temperature is too high, not only does the conversion of propylene or isobutylene become low, but the combustion of ammonia according to the following equation is also likely to occur vigorously during the ammoxidation of propylene or isobutylene:

$$4NH_3 + 3O_2 \rightarrow 2N_2 + 6H_2O.$$

It is also advantageous that the calcination time be in the range of from 1 to 5 hours. For selecting the most preferred calcination temperature and calcination time, it is desired to conduct experiments in which ammoxidation reactions are performed using catalyst compositions which have been prepared under various calcination conditions, thereby determining the most preferred calcination temperature and calcination time with reference to the results of the experiments, such as the conversion of propylene or isobutylene, the selectivity for desired acrylonitrile or methacrylonitrile, and the combustion ratio of ammonia.

Propylene, or isobutylene and ammonia to be used in the process of the present invention need not necessarily be of very high purity but may be of a commercial grade. Tert-butanol can also preferably be used instead of isobutylene. Molecular oxygen is usually employed in the form of air.

In the process of the present invention, it is advantageous that the volume ratios of propylene or isobutylene: ammonia: air be in the range of 1:0.9 to 1.3:7 to 11, preferably 1:1.0 to 1.2:8 to 10. The reaction temperature may be from 400 to 460° C., preferably from 410 to 440° C. The reaction may usually be conducted under a pressure of from atmospheric pressure to 3 atm. The time of contact between a gaseous mixture of raw materials and the catalyst composition (contact time) may be from 1 to 8 seconds, preferably from 2 to 6 seconds.

BEST MODE FOR CARRYING OUT THE INVENTION

Hereinbelow, the present invention will be described in more detail with reference to the following Reference Example, Examples and Comparative Examples, but they should not be construed as limiting the scope of the present invention.

Reference Example [Production of catalyst compositions A-1 to A-9 (Present invention) and B-1 to B-5 (Comparative)]

Catalyst composition A-1, composed of an oxide catalyst supported on 50% by weight, based on the total weight of the oxide catalyst and a silica carrier, of the silica carrier, having a structure represented by the formula:

$Mo_{12}Bi_{0.6}Fe_{2.0}Ni_{7.5}Cr_{0.2}In_{0.2}K_{0.2}O_x$ was prepared as follows.

A solution of 404.0 g of ammonium heptamolybdate $[(NH_4)_6Mo_7O_{24}\cdot 4H_2O]$ in 1200 g of water was added to 1667 g of a 30% silica sol while stirring.

To the resultant mixture was added a solution of 55.4 g of bismuth nitrate $[Bi(NO_3)_3\cdot 5H_2O]$, 154.6 g of iron nitrate $[Fe(NO_3)_3\cdot 9H_2O]$, 417.2 g of nickel nitrate $[Ni(NO_3)_2\cdot 6H_2O]$, 16.0 g of chromium nitrate $[Cr(NO_3)_3\cdot 9H_2O]$, 13.6 g of indium nitrate $[In(NO_3)_3\cdot 3H_2O]$ and 3.85 g of potassium nitrate $[KNO_3]$ in 600 g of a 13 wt % aqueous solution of nitric acid, to thereby obtain a slurry. The pH of the slurry was 0.3. The slurry thus obtained was fed to a centrifugation type spray-drying apparatus, in which the slurry was atomized by means of a sprayer having a dish type rotor disposed above the central portion of a dryer of the spray-drying apparatus, and dried while maintaining the entrance temperature of the dryer at 250° C. and the exit temperature of the dryer at 130° C., to thereby obtain a dried particulate catalyst precursor. The obtained dried particulate catalyst precursor was transferred to a kiln, in which the catalyst precursor was denitrified at 400° C. for 1 hour and then calcined at 560° C. for 2 hours, thereby obtaining a catalyst composition having an oxide catalyst supported on a silica carrier.

Catalyst compositions A-2 to A-9 and comparative catalyst compositions B-1 to B-5, having the respective compositions indicated in Table 1, were individually prepared in substantially the same manner as in Example 1. In preparing the above catalyst compositions, with respect to the sources of molybdenum, bismuth, iron, nickel, chromium, Indium, potassium and silica, the same materials as used for preparing catalyst composition A-1 were used. When it was intended to incorporate rubidium, cesium, manganese, magnesium, zinc, cerium, sodium and/or phosphorus in the catalyst compositions, rubidium nitrate $[RbNO_3]$, cesium nitrate $[CsNO_3]$, manganese nitrate $[Mn(NO_3)_2\cdot 6H_2O]$, magnesium nitrate $[Mg(NO_3)_2\cdot 6H_2O]$, zinc nitrate $[Zn(NO_3)_2\cdot 6H_2O]$, cerium nitrate $[Ce(NO_3)_2\cdot 6H_2O]$, sodium nitrate $[NaNO_3]$ and phosphoric acid $[H_3PO_4]$ were used as the sources of those elements. The calcination temperatures are shown in Table 1.

TABLE 1

| | Catalyst composition | Composition (atomic ratios) | | | | | | | weight % | Calcination temperature |
|---|---|---|---|---|---|---|---|---|---|---|
| | No. | Mo | Bi | Fe | Ni | Cr | In | A | E | SiO$_2$ | (° C.) |
| Present invention | A-1 | 12.0 | 0.6 | 2.0 | 7.5 | 0.2 | 0.2 | K$_{0.2}$ | — | 50.0 | 580 |
| | A-2 | 12.0 | 0.6 | 1.8 | 7.5 | 0.2 | 0.4 | K$_{0.2}$ | — | 50.0 | 570 |
| | A-3 | 13.0 | 0.6 | 1.8 | 5.5 | 0.2 | 0.4 | K$_{0.1}$Cs$_{0.2}$ | Mn$_{2.0}$ | 50.0 | 600 |
| | A-4 | 12.0 | 0.6 | 1.4 | 7.5 | 0.5 | 0.5 | K$_{0.2}$ | — | 50.0 | 560 |
| | A-5 | 12.0 | 0.6 | 0.8 | 7.5 | 0.6 | 0.8 | K$_{0.2}$ | — | 50.0 | 560 |
| | A-6 | 12.0 | 0.6 | 1.8 | 5.5 | 0.2 | 0.4 | K$_{0.2}$ | Mg$_{2.0}$ | 50.0 | 570 |
| | A-7 | 12.5 | 0.6 | 1.8 | 6.5 | 0.2 | 0.4 | Rb$_{0.2}$ | Zn$_{1.0}$ | 50.0 | 560 |
| | A-8 | 12.0 | 0.4 | 1.8 | 7.5 | 0.2 | 0.4 | K$_{0.2}$ | Ce$_{0.2}$ | 50.0 | 580 |
| | A-9 | 12.5 | 0.8 | 1.8 | 7.5 | 0.2 | 0.6 | K$_{0.4}$ | P$_{0.2}$Na$_{0.1}$ | 50.0 | 620 |
| Comparative | B-1 | 12.0 | 0.6 | 2.4 | 7.5 | — | — | K$_{0.2}$ | — | 50.0 | 570 |
| | B-2 | 12.0 | 0.6 | 1.4 | 7.5 | 1.0 | — | K$_{0.2}$ | — | 50.0 | 560 |
| | B-3 | 12.0 | 0.6 | 1.4 | 7.5 | — | 1.0 | K$_{0.2}$ | — | 50.0 | 560 |
| | B-4 | 12.0 | 0.6 | 1.4 | 5.4 | 1.2 | 1.2 | K$_{0.2}$ | — | 50.0 | 550 |
| | B-5 | 12.0 | 0.6 | 1.8 | 7.5 | 0.2 | 0.4 | — | — | 50.0 | 590 |

Examples 1 to 7 and Comparative Examples 1 to 5 (ammoxidation of propylene)

In Example 1, 50 cc of catalyst composition A-1 was charged in a fluidized bed reaction tube of Vycol glass having an inner diameter of 25 mm and having 12 steel nets of 10 mesh arranged at intervals of 1 cm. A gaseous mixture having a propylene content of 9% by volume (volume ratios of propylene: ammonia: oxygen: helium being 1:1.2:1.85:7.06) was flowed through the reaction tube at a flow rate of 3.50 cc/sec [0° C. under atmospheric pressure (N.T.P. conditions)]. The reaction pressure was maintained at atmospheric pressure, and the reaction temperature was maintained at 435° C. The results of the reaction were evaluated using three indices, namely, conversion of propylene, selectivity for acrylonitrile and acrylonitrile yield as defined by the following formulae. The values of these indices are shown in Table 2.

$$\text{Conversion }(C)\text{ of Propylene} = \frac{\text{mole of propylene reacted}}{\text{mole of propylene fed}} \times 100$$

$$\frac{\text{Selectivity }(S)}{\text{for Acrylonitrile}} = \frac{\text{mole of acrylonitrile formed}}{\text{mole of propylene reacted}} \times 100$$

$$\text{Acrylonitrile Yield }(Y) = \frac{\text{mole of acrylonitrile formed}}{\text{mole of propylene fed}} \times 100$$

Using catalyst compositions A-2 to A-7 and comparative catalyst compositions B-1 to B-5 individually, ammoxidation reactions of propylene were conducted in substantially the same manner as in Example 1. In each of the reactions, the content of propylene in the gaseous mixture of raw materials was fixed to 9% by volume, and the volume ratio of propylene: ammonia was fixed to 1:1.2. The volume ratio of propylene: oxygen was selected within the range of 1:1.8 to 1.9. The reaction temperature and the contact time were varied, depending on the reactivity of the catalyst composition used. The reaction conditions and results of the ammoxidations using above catalyst compositions are shown in Table 2.

$$\text{Contact time (sec)} = \frac{V}{F \times (273 + T)/273}$$

wherein:

V represents the amount (cc) of a catalyst;

F represents the flow rate (cc/sec) of the gaseous mixture of raw materials (in terms of the value under N.T.P. conditions); and T represents the reaction temperature (° C.).

Examples 8 to 9 and Comparative Example 6
(ammoxidation of isobutylene)

50 cc of catalyst composition A-3 was charged in the same reaction tube as used in the ammoxidation of propylene described above. The gaseous mixture having an isobutylene content of 7.5% by volume (volume ratios of isobutylene: ammonia: oxygen: water: helium being 1:1.2:1.95:1.8:7.38) was flowed through the tube at a flow rate of 3.88 cc/sec (in terms of the value under N.T.P. conditions). The reaction pressure was atmospheric pressure, and the reaction temperature was 430° C.

Using catalyst composition A-9 and comparative catalyst composition B-1 individually, substantially the same operation as mentioned above was conducted. The results of the reactions were evaluated using the conversion of isobutylene, the selectivity for methacrylonitrile and the methacrylonitrile yield as defined by substantially the same formulae as in the case of the ammoxidation of propylene, except that isobutylene is used in place of the propylene and methacrylonitrile is produced in place of the acrylonitrile. The reaction conditions and results of the ammoxidation are shown in Table 3.

TABLE 3

Ammoxidation of isobutylene

Pressure:atmospheric pressure
Gaseous mixture $C_4H_8:NH_3:O_2:He$ =
1.0(7.5%):1.20:1.9–2.0:1.8:Balance

| Example No. | Catalyst composition No. | Temperature (° C.) | Contact time (sec) | $O_2/$ $C_4H_8$ | Conversion (C) (%) | Selectivity (S) (%) | Yield (Y) (%) |
|---|---|---|---|---|---|---|---|
| Ex. 8 | A-3 | 430 | 5.0 | 1.95 | 99.5 | 79.6 | 79.2 |
| Ex. 9 | A-9 | 430 | 5.0 | 1.95 | 99.7 | 79.2 | 79.0 |
| Comp. 6 | B-1 | 430 | 5.0 | 1.95 | 99.7 | 77.0 | 76.8 |

Note: "Comp." indicates Comparative Example.

What is claimed is:

1. A process for producing acrylonitrile or methacrylonitrile, which comprises reacting propylene with, or reacting isobutylene with ammonia and molecular oxygen

TABLE 2

Ammoxidation of propylene

Pressure:atmospheric pressure
Gaseous mixture $C_3H_6:NH_3:O_2:He$ =
1.0(9.0%):1.20:1.8–1.9:Balance

| Example No. | Catalyst composition No. | Temperature (° C.) | Contact time (sec) | $O_2/C_3H_6$ | Conversion (C) (%) | Selectivity (S) (%) | Yield (Y) (%) |
|---|---|---|---|---|---|---|---|
| Ex. 1 | A-1 | 430 | 5.0 | 1.85 | 98.7 | 87.1 | 86.0 |
| Ex. 2 | A-2 | 430 | 5.0 | 1.85 | 98.8 | 87.9 | 86.8 |
| Ex. 3 | A-4 | 435 | 5.5 | 1.85 | 98.5 | 87.6 | 86.3 |
| Ex. 4 | A-5 | 435 | 5.5 | 1.85 | 98.3 | 87.6 | 86.1 |
| Ex. 5 | A-6 | 430 | 5.5 | 1.85 | 98.6 | 87.7 | 86.5 |
| Ex. 6 | A-7 | 430 | 5.5 | 1.88 | 98.2 | 87.5 | 85.9 |
| Ex. 7 | A-8 | 425 | 5.0 | 1.88 | 99.0 | 86.9 | 86.0 |
| Comp. 1 | B-1 | 430 | 5.0 | 1.88 | 98.5 | 85.4 | 84.1 |
| Comp. 2 | B-2 | 435 | 5.5 | 1.88 | 98.6 | 86.1 | 84.9 |
| Comp. 3 | B-3 | 435 | 5.5 | 1.88 | 98.8 | 85.5 | 84.5 |
| Comp. 4 | B-4 | 435 | 5.5 | 1.90 | 98.7 | 84.2 | 83.1 |
| Comp. 5 | B-5 | 420 | 4.8 | 1.90 | 99.6 | 82.9 | 82.6 |

Note: "Comp." indicates Comparative Example.

in the gaseous phase in the presence of an oxide catalyst composition comprising:

(a) an oxide catalyst represented by the following formula:

$$Mo_m Bi_b Fe_f Ni_n Q_q A_a E_e O_x \qquad (I)$$

wherein:

Q is a mixture of chromium and indium,

A is at least one element selected from the group consisting of potassium, rubidium and cesium, E is at least one element selected from the group consisting of manganese, magnesium, zinc, cerium, sodium and phosphorus, and m, b, f, n, q, a, e and x are the relative atomic ratios of molybdenum, bismuth, iron, nickel, Q, A, E and oxygen, respectively, wherein
m is a number of from 10 to 14,
b is a number of from 0.1 to 3,
f is a number of from 0.1 to 3,
n is a number of from 4 to 10,
q is a number of from 0.1 to 2,
a is a number of from 0.01 to 0.5,
e is a number of from 0 to 3, and
x is determined by the valence requirements of the other elements present; and (b) a silica carrier having said oxide catalyst supported thereon, wherein said silica carrier is present in an amount of from 40 to 60% by weight, based on the total weight of said oxide catalyst and said silica carrier.

2. The process according to claim 1, wherein E is at least one element selected from the group consisting of zinc and cerium.

3. The process according to claim 1 or 2, wherein the ratio of q to the sum of q and f is from 0.1 to 0.7.

4. The process according to any one of claims 1 to 3, wherein the atomic ratio of chromium to the sum of chromium and indium in Q is from 0.1 to 0.9.

* * * * *